United States Patent

Voit et al.

[11] Patent Number: 5,904,814
[45] Date of Patent: May 18, 1999

[54] REMOVAL OF WATER AND AMMONIA FROM BENZOPHENONE IMINE REACTOR EFFLUENTS

[75] Inventors: Guido Voit, Schriesheim; Matthias Dernbach, Eppelheim; Karl Beck, Östringen; Martin Holderbaum, Birkenfeld; Hans-Jürgen Weyer, Bobenheim-Roxheim, all of Germany

[73] Assignee: BASF Aktiengesellschaft, Ludwigshafen, Germany

[21] Appl. No.: 08/951,124

[22] Filed: Oct. 15, 1997

[30] Foreign Application Priority Data

Oct. 15, 1996 [DE] Germany ............... 196 42 541

[51] Int. Cl.$^6$ .................. B01D 3/00; C07C 249/02
[52] U.S. Cl. .................. 203/12; 95/902; 203/14; 203/89; 564/269
[58] Field of Search .................. 203/14, 12, 91, 203/29, 89; 34/345, DIG. 1; 564/249, 269; 210/689, 691; 95/902; 423/352

[56] References Cited

U.S. PATENT DOCUMENTS 4,130,586 12/1978 Isshiki et al. ............... 564/269
4,751,326 6/1988 Nawata et al. ............... 564/249
5,679,855 10/1997 Voit et al. ............... 564/269

FOREIGN PATENT DOCUMENTS 713 861 11/1995 European Pat. Off. .
359035021 2/1984 Japan .

OTHER PUBLICATIONS

Verardo et al., *Synthetic Communications*, vol. 18, No. 13, 1988, pp. 1501–1511.

*Primary Examiner*—Virginia Manoharan
*Attorney, Agent, or Firm*—Keil & Weinkauf

[57] ABSTRACT

A process for removing water and ammonia from benzophenone imine reactor effluents resulting from the catalytic reaction of benzophenones of the formula I

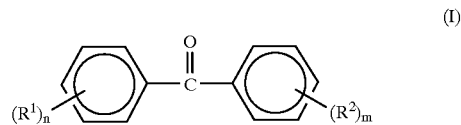

where $R^1$ and $R^2$, have the meaning stated in the specification and wherein ammonia is distilled off from effluents and wherein water is either distilled off from the effluents over removed non-distillatively.

9 Claims, No Drawings

REMOVAL OF WATER AND AMMONIA FROM BENZOPHENONE IMINE REACTOR EFFLUENTS

The present invention relates to a process for removing water and ammonia from benzophenone imine reactor effluents.

Various synthetic methods are known for preparing benzophenone imines. Besides the preparation by reaction of Grignard reagents with nitriles, followed by hydrolysis of the reaction product, or reaction of geminal dihalides with liquid ammonia, catalytic reactions of benzophenone with ammonia to give benzophenone imine and water are used in particular.

The catalysts used here are not only organic acids, ion exchangers and chlorides, such as iron(III) chloride, ammonium chloride and zinc(II) chloride, but also metal oxides, such as thorium oxide/silica or oxides of metals of the second to fifth ranks of the third to fifth main groups of the Periodic Table of the elements.

The reaction is preferably carried out with liquid ammonia, giving high yields.

The reaction of benzophenone and ammonia to give benzophenone imine gives equimolar amounts of benzophenone imine and water. Until now, this reactor effluent has generally not been worked up. Thus, U.S. Pat. No. 4,130,586 describes a process for preparing benzophenone imines where the resulting reactor effluent is diluted with benzene. No further work-up is described.

G. Verardo and A. G. Giumanini, in Synthetic Communications, 18 (13), (1988), 1501–1511, describe the preparation of ketimines from ketones and ammonia, ammonium chloride being used as catalyst. The reaction mixture is worked up by pouring it into water and ether, the organic layer being separated off and dried over sodium sulfate. A solution of hydrogen chloride in dry ether is then introduced, and the precipitated iminium salt is collected. This work-up method requires the use of organic solvents, making it generally unsuitable for industrial use. In addition, the iminium salt, and not the imine, is isolated.

There is no known industrially applicable work-up method for benzophenone imine reactor effluents.

It is also known from the literature that ketimines are hydrolyzed by alkaline solutions to give ketones.

It has now been found that, when a water-containing benzophenone imine reactor effluent is stored, a reverse reaction giving benzophenone and ammonia takes place to a considerable extent, which can amount to about 2% per week for storage at 40° C. It is therefore necessary to separate off the water contained in the reactor effluent if the benzophenone imine is to have adequate stability when stored.

It is an object of the present invention to provide a process for removing water and ammonia from benzophenone imine reactor effluents which can be carried out on an industrial scale and during which there is no reverse reaction to give benzophenone.

We have found that this object is achieved by means of a process for removing water and ammonia from benzophenone imine reactor effluents resulting from the catalytic reaction of benzophenones of the formula I

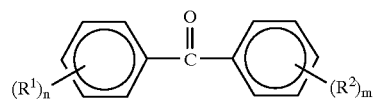

where $R^1$ and $R^2$, independently, are
a) halogen, hydroxyl, nitro, amino;
b) straight-chain, branched or cyclic alkyl or O-alkyl having from 1 to 12 carbon atoms, which may themselves be substituted with $C_{6-10}$-aryl, F, Cl, Br;
c) aryl or O-aryl having from 6 to 10 carbon atoms, which may themselves be substituted with $C_{1-12}$-alkyl or —O-alkyl;
d) heteroalkyl in which alkyl radicals defined as above are interrupted by one or more heteroatoms selected from the class consisting of O, S and N;
e) heteroaryl having from 5 to 10 ring atoms including from 1 to 3 heteroatoms selected from the class consisting of O, S and N,
where m and n, independently, are integers from 0 to 5, with ammonia,
where the ammonia is distilled off and the water is distilled off or removed non-distillative, preferably by using a drying agent.

It was found here that distillative removal of ammonia and water from benzophenone imine reactor effluents is possible without the occurrence to any significant extent of the abovementioned reverse reaction of the benzophenone imine to give benzophenone. Especially if the reaction is carried out with little exposure to high temperatures, the reverse reaction, which occurs to a greater extent at high temperature, is either prevented or largely suppressed.

Typical reactor effluents from the catalytic reaction of benzophenones with ammonia to give benzophenone imines comprise about 82% of benzophenone imine, about 4% of benzophenone, about 9% of water and about 5% of ammonia. This is the case in particular in a synthesis from benzophenone and liquid ammonia on $TiO_2$ as catalyst.

Some of the water and of the ammonia here forms an aqueous phase, which separates from the organic phase. The aqueous phase comprises, based on the total amount of the reactor effluent, about 7% by weight of water produced in the reaction and about 2% by weight of ammonia. The remaining approximately 2% by weight of water and approximately 3% by weight of ammonia here stay dissolved in the organic phase, composed of benzophenone imine and benzophenone.

In one embodiment of the invention, the benzophenone imine reactor effluent is used directly in the distillation.

A preferred embodiment provides that, before the distillation, the reactor effluent is separated by phase into an ammonia-containing aqueous phase and an organic phase, which still contains water and ammonia, and the aqueous phase is removed. The resulting mixture, which comprises essentially benzophenone imine, benzophenone, ammonia and water, is then fed to the distillation.

The distillation is preferably carried out at from 20 to 200° C. and at a pressure of from 1 to 1000 mbar.

In one embodiment of the invention, ammonia and water are distilled off simultaneously in the same distillation apparatus, simplifying the work-up process and avoiding high equipment costs. The distillation is carried out in such a way that there is very little exposure of the reactor effluent to high temperatures, in order to prevent a reverse reaction of the benzophenone imine to give benzophenone. For this reason in particular, the operation is carried out at reduced pressure. The distillation is preferably carried out in a stripping column or a film evaporator.

In one embodiment of the invention, the distillation is carried out using a stripping column. Water and ammonia are removed as overhead product at a column temperature of preferably from 20 to 200° C., particularly preferably from 50 to 100° C., and at a pressure of preferably from 100 to 1000 mbar, particularly preferably from 200 to 500 mbar, by stripping with an inert gas, preferably nitrogen, and the benzophenone imine, which is free of water and ammonia, is obtained as bottom product. The residence time in the distillation vessel is of the order of seconds. No decomposition of the benzophenone imine occurs.

In a particularly preferred embodiment of the invention, the distillation is carried out in a film evaporator and, depending on the evaporation conditions, the benzophenone imine can be obtained as bottom product or as distillate. At a starting oil temperature of preferably from 80 to 200° C., particularly preferably from 100 to 160° C., in particular from 100 to 130° C., and at a pressure of preferably from 5 to 200 mbar, particularly preferably from 20 to 100 mbar, the benzophenone imine is obtained as high-boiling or bottom product. The residence time in the film evaporator here is of the order of seconds and is preferably shorter than for the stripping column. At a starting oil temperature of preferably from 150 to 200° C., particularly preferably from 160 to 180° C., and at a pressure of preferably from 1 to 20 mbar, particularly preferably from 5 to 15 mbar, the benzophenone imine is drawn off as overhead product. The benzophenone imine obtained here is free of water. In both procedures, water and ammonia are removed via the vacuum system. The residence time in the film evaporator here is very short.

In a further embodiment of the invention, ammonia and water are separated off sequentially. It is preferable to separate off firstly ammonia and then water, the ammonia being separated off preferably by a distillative method, and the water being separated off by a distillative or non-distillative method.

The water is preferably removed by a non-distillative method, in particular using a drying agent after the ammonia has been distilled off.

For this, the ammonia is preferably firstly removed from the reaction mixture using a falling-film evaporator, the oil temperature of the evaporator being preferably from 60 to 200° C., particularly preferably from 80 to 140° C., in particular from 80 to 120° C. The pressure is preferably from 5 to 200 mbar, particularly preferably from 20 to 100 mbar, in particular from 20 to 60 mbar. The residence time in the falling-film evaporator here is of the order of seconds.

The removal of the water is preferably carried out by a distillative method. For non-distillative removal of water, the reactor effluents, in particular the benzophenone imines, should be in liquid form preferably at 25° C. or room temperature. In the case of higher-melting benzophenone imines, it is possible to operate at a correspondingly higher temperature, but there should be very little exposure to high temperatures.

In one embodiment, the benzophenone imine reactor effluent which has been freed from ammonia is freed from water by a non-distillative method, by treatment with drying agents. Examples of drying agents which can be used here are alkali metal sulfates and alkaline-earth metal sulfates, in particular magnesium sulfate or sodium sulfate, and also molecular sieves.

Preference is given to the use of a molecular sieve, for example of type 514, 4 Å.

In one embodiment of the invention, the benzophenone imine reactor effluent (raw benzophenone imine) which has been freed from ammonia here is freed from water in a continuous process by alternating operation of two molecular sieve columns. The effluent is continuously passed through a first column filled with molecular sieve, the residence time being selected so that there is complete removal of water. As soon as water is detected in the benzophenone imine eluate from the column, i.e. as soon as the capacity of the molecular sieve is exhausted, the reactor effluent is passed through a second molecular sieve column. During this period, the molecular sieve which was used in the first column and is loaded with water can be regenerated, for example by heating. By alternating the operation of the two columns, it is possible for the procedure to operate continuously.

The novel process for removing water and ammonia from benzophenone imine reactor effluents is suitable for benzophenone imine reactor effluents of any desired water and ammonia content. It is possible to use any reactor effluents from any known synthetic method for preparing benzophenone imines by catalytic reaction of benzophenones with ammonia.

The benzophenone imines or benzophenone imine/benzophenone mixtures obtained according to the invention are essentially free of ammonia and water. The water content of the resulting benzophenone imines is preferably below 0.07% by weight, particularly preferably below 0.03% by weight, based on the entire mixture. The benzophenone imine or benzophenone imine/benzophenone mixture obtained in this way is thus stable in storage. Room-temperature stability studies of the essentially water-free benzophenone imine obtained in this way showed no gas-chromatographically detectable reverse reaction or decomposition of the benzophenone imine.

The resulting benzophenone imine or benzophenone imine/benzophenone mixture, which is essentially free of water and ammonia, is virtually colorless. The APHA color number is generally in the range from 20 to 50 Hazen in measurements according to DIN ISO 6271.

In the distillative work-up of the benzophenone imine reactor effluents, it is preferable that any exposure to high temperatures is kept to a sufficiently low level to give a colorless benzophenone imine.

Benzophenone imine reactor effluents which can be used according to the invention comprise benzophenone imines of the formula (II)

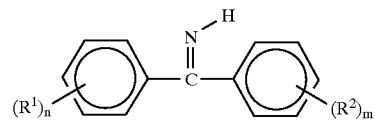

prepared by catalytic reaction of benzophenones of the formula (I)

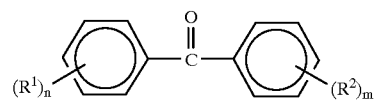

where $R^1$ and $R^2$, independently, are
  a) halogen, hydroxyl, nitro, amino;
  b) straight-chain, branched or cyclic alkyl or O-alkyl having from 1 to 12 carbon atoms, which may themselves be substituted with $C_{6-10}$-aryl, F, Cl, Br;

c) aryl or O-aryl having from 6 to 10 carbon atoms, which may themselves be substituted with $C_{1-12}$-alkyl or —O-alkyl;

d) heteroalkyl in which alkyl radicals defined as above are interrupted by one or more heteroatoms selected from the class consisting of O, S and N;

e) heteroaryl having from 5 to 10 ring atoms including from 1 to 3 heteroatoms selected from the class consisting of O, S and N, where m and n, independently, are integers from 0 to 5, with ammonia.

$R^1$ and $R^2$, independently of one another, are preferably hydroxyl, nitro, straight-chain or branched alkyl or O-alkyl having from 1 to 4 carbon atoms, or phenyl or O-phenyl, which may be unsubstituted or substituted with $C_{1-4}$-alkyl or $C_{1-4}$-O-alkyl.

m and n, independently, are preferably integers from 0 to 2, particularly preferably 0 or 1.

In particular, m=n=0, i.e. benzophenone is used for reaction with ammonia to give benzophenone imine.

The invention is illustrated below by means of examples.

The benzophenone imine reactor effluent used in the examples was obtained by the following process.

180 g of benzophenone and 720 g of ammonia per hour were passed, at a pressure of 200 bar and at 130° C., through a tubular reactor filled with 60 ml of titanium dioxide in the form of 3 mm extrudates. The aqueous phase was then separated off from the reactor effluent, and the organic phase was used in the following examples. This organic phase consisted of 89.8% by weight of benzophenone imine, 5.28% by weight of benzophenone, 1.82% by weight of water and 3.10% by weight of ammonia.

EXAMPLE 1

500 g of the benzophenone imine effluent were pumped continuously to a film evaporator with an oil temperature of from 100 to 120° C. and a pressure of 9 mbar. This gave, as bottom product, a total of 441 g of anhydrous, colorless benzophenone imine mixture having a content of 94.3% by weight of benzophenone imine and 5.68% by weight of benzophenone. The product had an APHA color number of 35 Hazen. The water content, determined by the Karl Fischer method, cf. DIN 51777, Part 1, direct method, was 0.03% by weight.

EXAMPLE 2

500 g of the benzophenone imine effluent were distilled continuously through a film evaporator with an oil temperature of from 160 to 180° C., at a pressure of less than 10 mbar. This gave, as product at the top of the column, a total of 422 g of anhydrous, colorless benzophenone imine mixture having a benzophenone imine content of 94.3% by weight and a benzophenone content of 5.56% by weight. The product had an APHA color number of 28 Hazen. The water content, determined by the Karl Fischer method, was 0.02% by weight.

EXAMPLE 3

250 g of the benzophenone imine effluent were pumped continuously to a falling-film evaporator with an oil temperature of 100° C., at a pressure of 40 mbar, to remove the ammonia. This gave, as bottom product, 228 g of ammonia-free raw benzophenone imine. This product had a water content of about 1.6% by weight, and was mixed with 47 g of molecular sieve (type 514, 4 Å), and stirred at room temperature. After 4 hours, the molecular sieve was filtered off, giving 214 g of colorless benzophenone imine mixture having a benzophenone imine content of 94.1% by weight and a benzophenone content of 5.79% by weight. The APHA color number was 22 Hazen and the water content, determined by the Karl Fischer method, was 0.6% by weight.

In Examples 1 and 2, the ratio of benzophenone to benzophenone imine was equal to the ratio in the reactor effluent used, and in Example 3 it was slightly higher. This shows that during the work-up there is no, or only very little, reverse reaction or decomposition of the benzophenone imine. The novel process may therefore advantageously be used for purifying benzophenone imine reactor effluents in order to obtain a product which can be stored.

Benzophenone imine is used in industry as a starting compound for products which give protection from light.

We claim:

1. A process for removing water and ammonia from benzophenone imine reactor effluents resulting from the catalytic reaction of benzophenones of the formula I

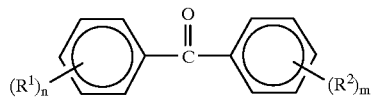

(I)

where $R_1$ and $R^2$, are independently selected from the group consisting of a) halogen, hydroxyl, nitro, amino;

b) straight-chain, branched or cyclic alkyl or O-alkyl having from 1 to 12 carbon atoms, which may themselves be substituted with $C_{6-10}$-aryl, F, Cl, Br;

c) aryl or O-aryl having from 6 to 10 carbon atoms, which may themselves be substituted with $C_{1-12}$-alkyl or —O-alkyl;

d) heteroalkyl in which alkyl radicals defined as above are interrupted by one or more heteroatoms selected from the class consisting of O, S and N; and e) heteroaryl having from 5 to 10 ring atoms including from 1 to 3 heteroatoms selected from the class consisting of O, S and N, where m and n, independently, are integers from 0 to 5, with ammonia, which process comprises: distilling off the ammonia and removing the water by distillation or removing the water non-distillatively.

2. The process of claim 1, wherein said ammonia and water are distilled off simultaneously.

3. The process of claim 1, wherein the ammonia is first distilled off from the reactor effluent and then the water is distilled off or removed non-distillatively.

4. The process of claim 3, wherein the non-distillative removal of the water is carried out with a drying agent.

5. The process of claim 3, wherein the ammonia is distilled using a falling-film evaporator.

6. The process of claim 5, wherein the water is removed using a molecular sieve.

7. The process of claim 1, wherein, before the distillation, the reactor effluent is separated by phase into an ammonia-containing aqueous phase and an organic phase, which still contains water and ammonia, and the aqueous phase is removed.

8. The process of claim 1, wherein the distillation is carried out in a stripping column or in a film evaporator.

9. The process of claim 1, wherein the distillation is carried out at from 20 to 200° C. and at a pressure of from 1 to 1000 mbar.

* * * * *